(12) United States Patent
Kolen et al.

(10) Patent No.: US 11,759,176 B2
(45) Date of Patent: *Sep. 19, 2023

(54) ULTRASOUND IMAGE PROCESSING

(71) Applicant: KONINKLIJKE PHILIPS N.V., Eindhoven (NL)

(72) Inventors: Alexander Franciscus Kolen, Eindhoven (NL); Harm Jan Willem Belt, Weert (NL); Godefridus Antonius Harks, Rijen (NL); Gerardus Henricus Maria Gijsbers, Liempde (NL); Hong Liu, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 119 days.

This patent is subject to a terminal disclaimer.

(21) Appl. No.: 17/534,638

(22) Filed: Nov. 24, 2021

(65) Prior Publication Data

US 2022/0079560 A1     Mar. 17, 2022

Related U.S. Application Data

(63) Continuation of application No. 16/646,648, filed as application No. PCT/EP2018/074352 on Sep. 10, 2018, now Pat. No. 11,213,276.

(30) Foreign Application Priority Data

Sep. 14, 2017 (EP) .................................. 17191027

(51) Int. Cl.
*G06K 9/00* (2022.01)
*A61B 8/00* (2006.01)
(Continued)

(52) U.S. Cl.
CPC .............. *A61B 8/463* (2013.01); *A61B 5/066* (2013.01); *A61B 8/0841* (2013.01);
(Continued)

(58) Field of Classification Search
USPC ........ 382/100, 106–107, 123, 128–132, 154, 382/162, 168, 173, 181, 191, 199, 219,
(Continued)

(56) References Cited

U.S. PATENT DOCUMENTS 6,515,657 B1   2/2003  Zanelli
8,795,178 B2 * 8/2014  Hansegard ........... A61B 8/0841
                                                600/440
(Continued)

FOREIGN PATENT DOCUMENTS

EP          2064991 A2      6/2009

OTHER PUBLICATIONS

International Search Report and Written Opinion for International Application No. PCT/EP2018/074352, filed Sep. 10, 2018, 12 pages.

*Primary Examiner* — Seyed H Azarian

(57) ABSTRACT

A method for ultrasound image processing having steps of receiving sequences of ultrasound images imaging an anatomical feature of interest during two cardiac cycles one in the absence of, and the other in the presence of, an invasive medical device in said ultrasound images, each ultrasound image corresponding to a different phase of said cardiac cycle. The invasive medical device may at least partially obscure the anatomical feature of interest for each ultrasound image of the further sequence. The location of the invasive medical device is tracked and isolated in the ultrasound image, and the isolated invasive medical device is inserted into an ultrasound image of the first sequence of a corresponding phase of the cardiac cycle in the tracked
(Continued)

location. The method also controls a display device to display the first sequence of ultrasound images including the inserted invasive medical device.

5 Claims, 7 Drawing Sheets

(51) Int. Cl.
  *G06T 7/70* (2017.01)
  *A61B 5/06* (2006.01)
  *A61B 8/08* (2006.01)
  *A61B 8/12* (2006.01)
  *G06T 7/00* (2017.01)
  *G06T 7/20* (2017.01)
  *G06T 7/60* (2017.01)
  *G06T 11/00* (2006.01)

(52) U.S. Cl.
  CPC .............. *A61B 8/0883* (2013.01); *A61B 8/12* (2013.01); *G06T 7/0012* (2013.01); *G06T 7/20* (2013.01); *G06T 7/60* (2013.01); *G06T 7/70* (2017.01); *G06T 11/00* (2013.01); *G06T 2200/24* (2013.01); *G06T 2207/10016* (2013.01); *G06T 2207/10132* (2013.01); *G06T 2207/30004* (2013.01)

(58) Field of Classification Search
  USPC ........ 382/220, 254, 275–276, 286–305, 321; 600/424, 439, 478; 378/4, 21
  See application file for complete search history.

(56) References Cited

U.S. PATENT DOCUMENTS

| | | | |
|---|---|---|---|
| 9,301,733 B2* | 4/2016 | Gerard | A61B 8/466 |
| 2007/0167801 A1 | 7/2007 | Webler et al. | |
| 2008/0167801 A1 | 7/2008 | Geelen et al. | |
| 2009/0005679 A1 | 1/2009 | Dala-Krishna | |
| 2012/0059249 A1* | 3/2012 | Verard | A61B 6/463 600/424 |
| 2014/0100439 A1 | 4/2014 | Jones et al. | |
| 2015/0342530 A1* | 12/2015 | Dekker | A61B 1/051 600/478 |
| 2016/0089116 A1 | 3/2016 | Duncan et al. | |
| 2019/0307412 A1* | 10/2019 | Dascal | A61B 6/5247 |
| 2020/0273182 A1* | 8/2020 | Raudins | A61B 5/7285 |

* cited by examiner

ULTRASOUND IMAGE PROCESSING

RELATED APPLICATIONS

This application is a continuation of co-pending U.S. patent application Ser. No. 16/646,648, filed on Mar. 12, 2020, which in turn is the U.S. National Phase application under 35 U.S.C. § 371 of International Application No. PCT/EP2018/074352, filed on Sep. 10, 2018, which claims priority to and the benefit of European Application No. 17191027.6, filed Sep. 14, 2017. These applications are hereby incorporated by reference herein.

FIELD OF THE INVENTION

The present invention relates to an ultrasound image processing apparatus comprising an image processor arrangement adapted to receive and process a plurality of ultrasound images.

The present invention further relates to an ultrasound imaging system comprising such an ultrasound image processing apparatus.

The present invention still further relates to a computer program product for configuring an ultrasound image processing apparatus.

BACKGROUND OF THE INVENTION

Ultrasound imaging is rapidly gaining popularity as an imaging technique supporting interventional procedures, either as a standalone technique or in combination with other imaging techniques such as x-ray imaging techniques. During such interventional procedures, an invasive medical device such as a catheter, guide wire, needle, and so on, is inserted into a patient by a medical professional, with the imaging tools such as ultrasound imaging being used to guide the invasive medical device towards or past anatomical regions of interest within the patient. In particular, 3-D or volumetric ultrasound imaging is a powerful tool to assist the medical professional in guiding the invasive medical device through the patient's anatomy.

A common problem during such interventional procedures is that part of an anatomical feature of interest of the patient may be blocked from view by the invasive medical device. This typically occurs in a situation where the invasive medical device is located in between the ultrasound transducer or probe and the anatomical feature of interest, in which case the invasive medical device can cast an acoustic shadow onto the anatomical feature of interest, thereby yielding an incomplete view of the anatomical feature of interest. This is of course undesirable, as it hampers the medical professional in the correct operation or guidance of the invasive medical device relative to the incompletely imaged anatomical feature of interest.

Solutions exist to address the problem of such acoustic shadowing of part of an anatomical region of interest. For example, US 2014/0100439 A1 discloses a method and system for the removal of guidewire artefacts from ultrasound images. At least two ultrasound images of an imaging surface are acquired. Each acquired ultrasound image comprises a set of data. A guidewire artefact is detected in one of the at least two images. The guidewire artefacts is replaced with data representing the imaging surface obtained from another one of the at least two images.

This technique assumes that the imaging surface is the same between the different acquired ultrasound images. This, however, often is an oversimplification that can lead to incorrect artefact removal. Many invasive medical devices are inserted into the patient's cardiovascular system, e.g. to access the patient's heart or arteries. As is well-known per se, the cardiac cycle consists of different phases, e.g. expansion and contraction phases, during which various parts of the cardiovascular system, most notably the heart, change shape. Consequently, it is not straightforward to correct shadow artefacts in ultrasound images of an anatomical feature of interest that changes shape during the cardiac cycle, as the changes in the geometry of the anatomical feature of interest can cause the introduction of artefacts in a composite ultrasound image in which parts of different ultrasound images captured during such a cardiac cycle are combined due to different parts of the anatomy being combined in such a composite ultrasound image.

SUMMARY OF THE INVENTION

The present invention seeks to provide an ultrasound image processing apparatus that is configured to remove shadow regions from such imaged anatomical regions of interest in a more robust manner.

The present invention further seeks to provide an ultrasound imaging system comprising such an ultrasound image processing apparatus.

The present invention still further seeks to provide a computer program product for configuring such an ultrasound image processing apparatus.

According to an aspect, there is provided an ultrasound image processing apparatus comprising an image processor arrangement adapted to receive a first sequence of ultrasound images imaging an anatomical feature of interest during a first full cardiac cycle in the absence of an invasive medical device in said ultrasound images, each ultrasound image corresponding to a different phase of said cardiac cycle; receive a further sequence of ultrasound images imaging the anatomical feature of interest during a further full cardiac cycle in the presence of the invasive medical device in said ultrasound images, each ultrasound image corresponding to a different phase of said cardiac cycle said invasive medical device at least partially obscuring the anatomical feature of interest, and for each ultrasound image of the further sequence: track the location of the invasive medical device in the ultrasound image; isolate the invasive medical device from the ultrasound image; and insert the isolated invasive medical device into an ultrasound image of the first sequence of a corresponding phase of the cardiac cycle in the tracked location; and control a display device to display the first sequence of ultrasound images including the inserted invasive medical device.

In this manner, a sequence of ultrasound images is generated in which a historical view of the anatomical feature of interest is merged with an actual view of the invasive medical instrument such as a catheter, guide wire, needle or the like, in front of the anatomical feature of interest. This results in a sequence of ultrasound images, e.g. a cine loop or the like, in which the anatomical feature of interest is fully visible without acoustic shading by the invasive medical device blocking part of view of the anatomical feature of interest.

The ultrasound image processing apparatus may be adapted to trigger the capture of at least the further sequence of ultrasound images in response to an external stimulus indicative of a particular point in the cardiac cycle to ensure that each sequence of ultrasound images captured with an ultrasound probe is initiated at the same point in time of the cardiac cycle such that the ultrasound images in such sequences are all taken at set phases of the cardiac cycle.

In an embodiment, the image processor arrangement is adapted to determine the location of the invasive medical device in an ultrasound image of the further sequence using an object recognition algorithm. In this embodiment, the location of the invasive medical device is determined by processing the ultrasound images of the further sequence. For instance, the object recognition algorithm may be an optical shape sensing algorithm to detect the invasive medical device in the ultrasound images of the further sequence.

In an alternative embodiment, the invasive medical device comprises a plurality of electromagnetic transmitters in a defined alignment along the invasive medical device, e.g. ultrasound transmitters, wherein the image processor arrangement is adapted to determine the location of the invasive medical device in an ultrasound image of the further sequence based on received electromagnetic transmissions from said plurality of electromagnetic transmitters. In this embodiment, the location of the invasive medical device within the ultrasound images of the further sequence may be determined without having to analyse the ultrasound images, as the location information may be obtained using separate location detection techniques.

According to another aspect, there is provided an ultrasound imaging system comprising the ultrasound image processing apparatus according to any of the herein described embodiments and an ultrasound probe that can be communicatively coupled to the ultrasound image processing apparatus and is adapted to provide the ultrasound image processing apparatus with at least the further sequence of ultrasound images. Such an ultrasound imaging system benefits from being able to provide its user with improved quality ultrasound images during procedures in which the progress of an invasive medical instrument such as a catheter, guide wire, needle and so on relative to other anatomical feature of interest is being imaged using the ultrasound imaging system.

According to yet another aspect, there is provided a computer program product comprising a computer readable storage medium having computer readable program instructions embodied therewith for, when executed on the image processor arrangement of the ultrasound image processing apparatus of any of the herein described embodiments, cause the image processor arrangement to receive a first sequence of ultrasound images imaging an anatomical feature of interest during a first full cardiac cycle in the absence of an invasive medical device in said ultrasound images, each ultrasound image corresponding to a different phase of said cardiac cycle; receive a further sequence of ultrasound images imaging the anatomical feature of interest during a further full cardiac cycle in the presence of the invasive medical device in said ultrasound images, each ultrasound image corresponding to a different phase of said cardiac cycle said invasive medical device at least partially obscuring the anatomical feature of interest, and for each ultrasound image of the further sequence: track the location of the invasive medical device in the ultrasound image; isolate the invasive medical device from the ultrasound image; and insert the isolated invasive medical device into an ultrasound image of the first sequence of a corresponding phase of the cardiac cycle in the tracked location; and control a display device to display the first sequence of ultrasound images including the inserted invasive medical device.

Consequently, with such a computer program product the image processor arrangement of an ultrasound image processing apparatus may be configured to accurately remove shadow regions from an anatomical feature of interest that changes shape during different phases of the cardiac cycle such as a beating heart or another part of the cardiovascular system that changes shape during the cardiac cycle, as explained in more detail above.

The computer program product may further cause the image processor arrangement to trigger the capture of at least the further sequence of ultrasound images in response to an external stimulus indicative of a particular point in the cardiac cycle to ensure that the various sequences, e.g. cine loops, of ultrasound images are captured in a synchronized manner.

In an embodiment, the computer program product further causes the image processor arrangement to determine the location of the invasive medical device in an ultrasound image of the further sequence using an object recognition algorithm, such as an optical shape sensing algorithm. In this embodiment, the location of the invasive medical device is determined from the ultrasound images of the further sequence, thereby providing a method in which all necessary information is retrieved from the ultrasound images captured with the ultrasound probe.

In an alternative embodiment, the invasive medical device comprises a plurality of electromagnetic transmitters in a defined alignment along the invasive medical device, the computer program product further causing the image processor arrangement to determine the location of the invasive medical device in an ultrasound image of the further sequence based on received electromagnetic transmissions from said plurality of electromagnetic transmitters. This may facilitate a particularly fast determination of the location of the invasive medical device as the ultrasound images do not need to be evaluated to determine this location, which can be computationally intensive.

Such a computer program product for example may be used to reconfigure, e.g. upgrade, existing ultrasound image processing apparatuses.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

Figure 1:
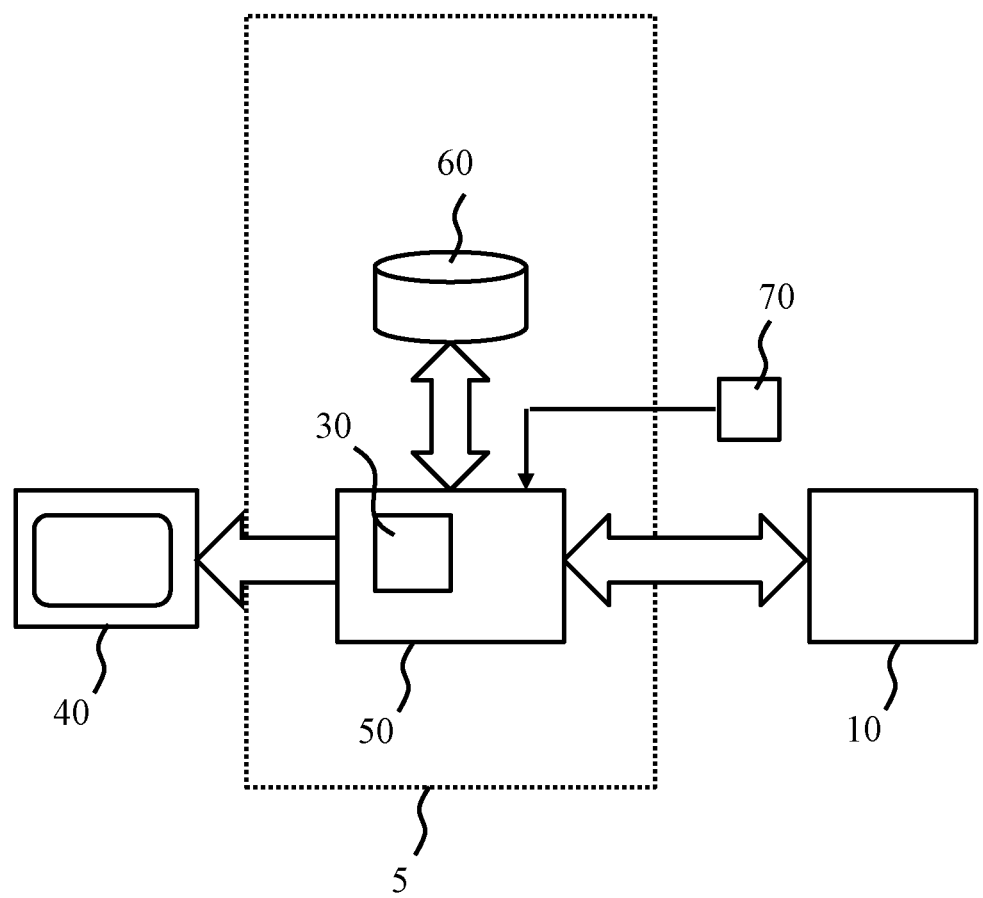
FIG. 1 schematically depicts an ultrasound image processing apparatus according to an embodiment.

It should be understood that the Figures are merely schematic and are not drawn to scale. It should also be understood that the same reference numerals are used throughout the Figures to indicate the same or similar parts.

FIG. 1 schematically depicts an ultrasound image processing apparatus 5 according to an example embodiment of the present invention. The ultrasound image processing apparatus 5 comprises an ultrasound image processor arrangement 50 at least including an image processor 30 although the ultrasound image processor arrangement 50 may comprise further processors as will be explained in more detail below by way of non-limiting example. The ultrasound image processor arrangement 50 may be communicatively coupled to a data storage arrangement 60, here shown as forming part of the ultrasound image processing apparatus 5 by way of non-limiting example only. It is for instance equally feasible that the data storage arrangement 60 is a remote data storage arrangement, e.g. a cloud-based data storage arrangement 60, which may be accessed by the ultrasound image processor arrangement 50 over a wired or wireless network, e.g. the Internet, a local area network, a mobile communications network, a point-to-point connection and so on, in which case the ultrasound image processing apparatus 5 further comprises a network interface (not shown), e.g. a wired network interface such as an Ethernet port or a wireless network interface such as a Bluetooth or Wi-Fi transceiver communicatively coupled to the ultrasound image processor arrangement 50 through which the ultrasound image processor arrangement 50 may communicate with the data storage arrangement 60. The data storage arrangement 60 may take any suitable shape, e.g. one or more memory devices, one or more magnetic storage disks, one or more solid state storage disks, one or more optical storage disks, and so on, or any combination thereof.

The ultrasound image processing apparatus 5 may further comprise a display device (from here on referred to as display) 40, or at least be adapted to provide a communicative coupling between the ultrasound image processor arrangement 50 and the display 40 such that an ultrasound image processing result generated with the ultrasound image processor arrangement 50 may be displayed on the display 40 under control of the ultrasound image processor arrangement 50.

Figure 2:
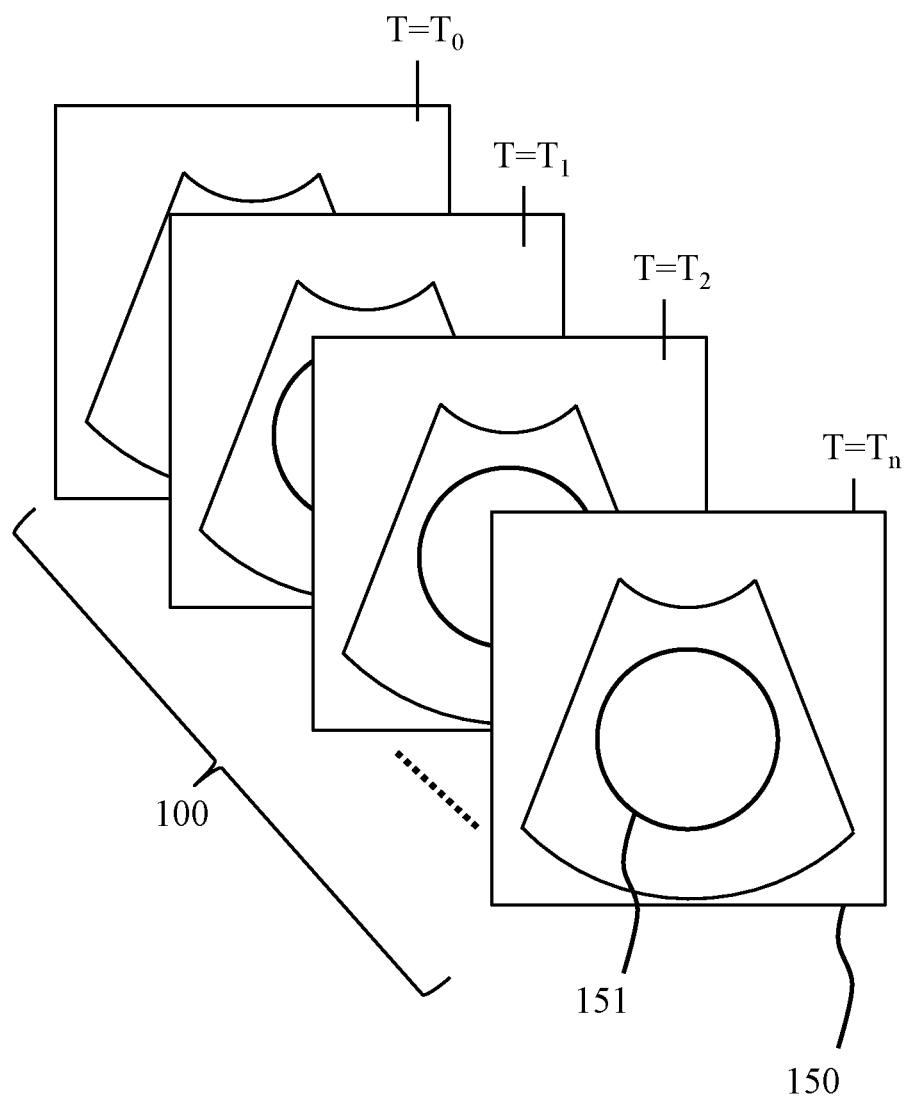
FIG. 2 schematically depicts an initial temporal sequence of ultrasound images for processing by such an ultrasound image processing apparatus.
Figure 5:
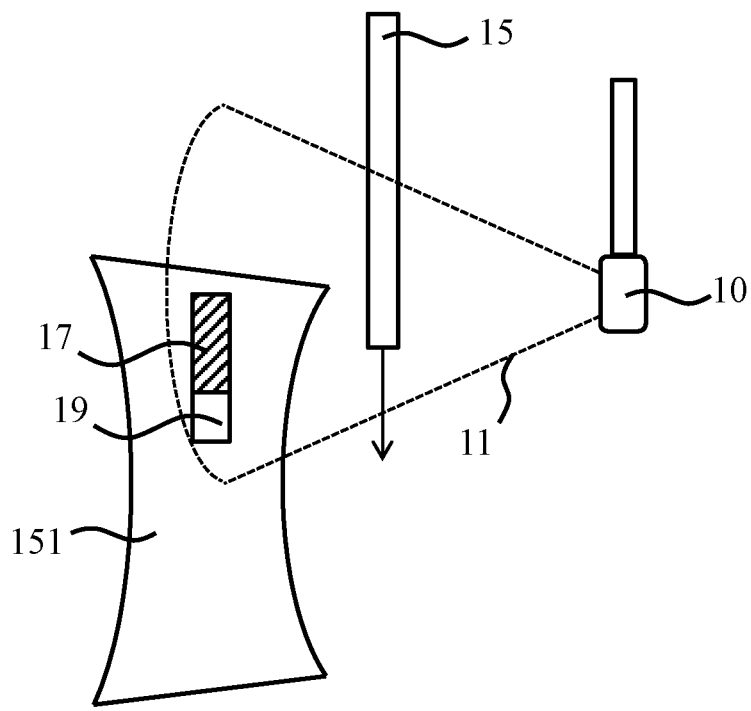
FIG. 5 schematically depicts an imaging arrangement during the further temporal sequence of ultrasound images.

The ultrasound image processing apparatus 5 is further adapted to provide a communicative coupling between the ultrasound image processor arrangement 50 and an ultrasound transducer 10, which typically is an ultrasound transducer for generating volumetric or 3-D ultrasound images. Such an ultrasound transducer 10 is well-known per se and is therefore not explained in further detail for the sake of brevity only. The ultrasound image processor arrangement 50 may receive a temporal sequence 100 of ultrasound images 150 as schematically depicted in FIG. 2. In the context of the present application, a temporal sequence 100 of ultrasound images 150 refers to a sequence of ultrasound images in which the same anatomical feature of interest 151 is imaged over a period of time (as depicted in FIG. 5 by the different time labels $T=T_0$, $T=T_1$, $T=T_2$, $T=T_n$), such that the sequence 100 comprises a plurality of ultrasound images 150 in which changes over time in the anatomical feature of interest can be visualized. This for example is particularly useful where the temporal sequence 100 of ultrasound images 150 images an anatomical feature of interest 151 undergoing shape changes during the cardiac cycle, e.g. having different shapes at different points or phases of the cardiac cycle, in which case each ultrasound image 150 captures the anatomical feature of interest 151 during a particular phase of the cardiac cycle. The anatomical feature of interest 151 may be the patient's beating heart or any other anatomical feature of interest 151, e.g. any other part of the cardiovascular system, undergoing shape changes during the cardiac cycle.

Each temporal sequence 100 typically constitutes a set of ultrasound images 150 imaging the anatomical feature of interest 151 over a full cardiac cycle, with different temporal sequences 100 imaging the anatomical feature of interest 151 during different cardiac cycles. For example, each temporal sequence may define a cine loop to be displayed on the display 40 by the ultrasound image processing apparatus 5. The ultrasound image processor arrangement 50 typically receives a plurality of such temporal sequences 10 of ultrasound images 150 of the anatomical feature of interest 151. The ultrasound image processor arrangement 50 may receive the temporal sequences 100 of ultrasound images 150 directly from the ultrasound transducer 10 or alternatively may receive the temporal sequences 100 of ultrasound images 150 from the data storage arrangement 60 into which the temporal sequences 100 of ultrasound images 150 were previously stored, e.g. by the ultrasound image processing apparatus 5 for processing at a later date. The temporal sequences 100 of ultrasound images 150 may consist of a sequence of 2-D ultrasound image frames, which may be acquired with a 2-D ultrasound transducer 10 although preferably the temporal sequences 100 of ultrasound images 150 comprise a sequence of volumetric ultrasound images 150.

In accordance with embodiments of the present invention, the ultrasound image processing apparatus 5 is adapted to receive a first sequence 100 of ultrasound images 150, in which each ultrasound image 150 captures a different phase of the patient's cardiac cycle imaged by the first sequence 100. In this first sequence 100, no invasive medical device is present in its ultrasound images 150 such that the anatomical feature of interest 151 is not in part obscured by an acoustic shadow region caused by such an interventional medical device blocking part of the ultrasound beam of an ultrasound probe used for the generation of the first sequence 100 of ultrasound images 150.

Figure 3:
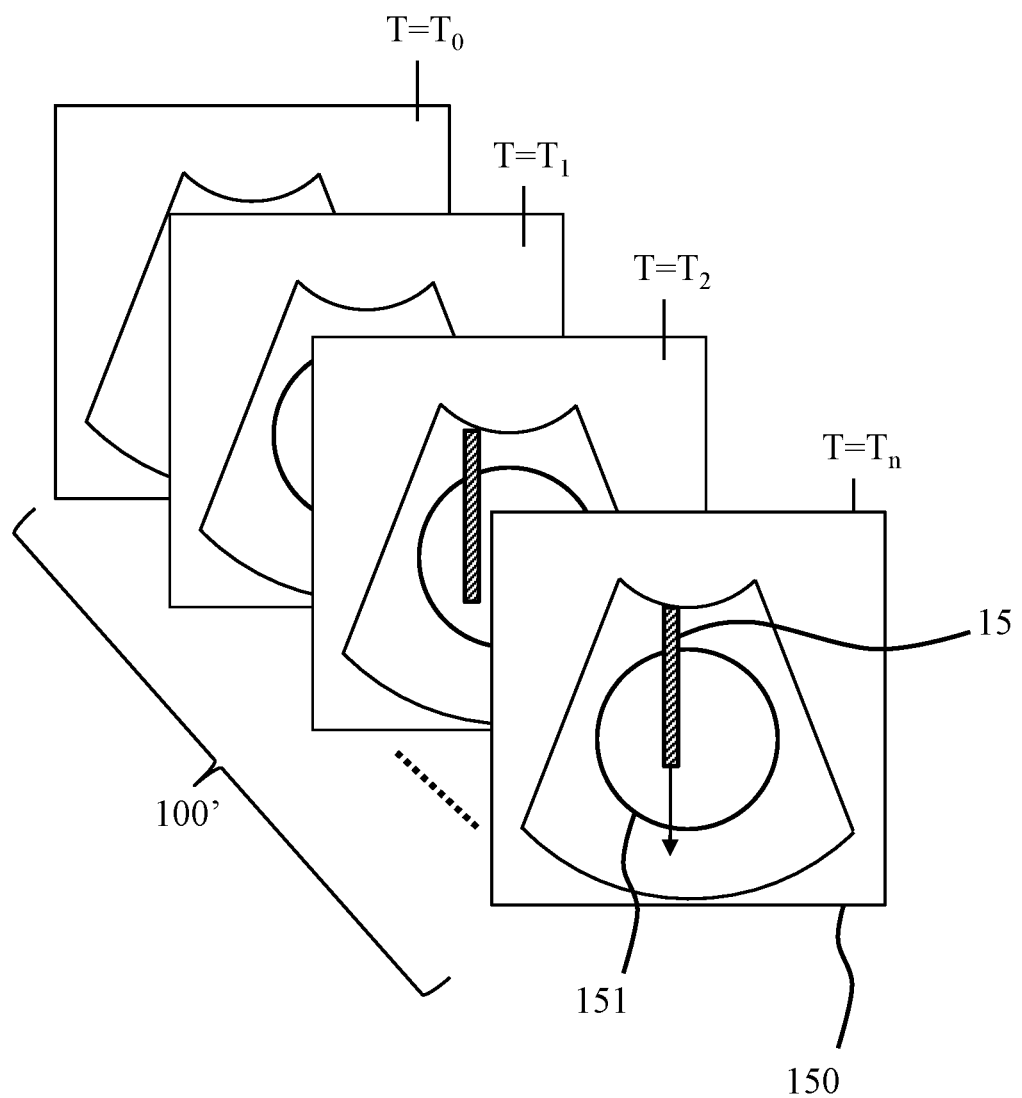
FIG. 3 schematically depicts a further temporal sequence of ultrasound images for processing by such an ultrasound image processing apparatus.

The ultrasound image processing apparatus 5 is further adapted to receive a further sequence 100' of ultrasound images 150, in which each ultrasound image 150 also captures a different phase of the patient's cardiac cycle imaged by the further sequence 100', as schematically depicted in FIG. 3. The further sequence 100' of ultrasound images 150 is distinguished from the first sequence 100 of ultrasound images 150 by the presence of an invasive medical device 15 in the field of view of the anatomical feature of interest 151, such that part of the anatomical feature of interest 151 is obscured from view by an acoustic shadow region generated by the invasive medical device 15 blocking part of the ultrasound waves generated by the ultrasound probe. As will be understood, the first sequence 100 and the further sequence 100' of ultrasound images 150 typically image a full cardiac cycle (or a plurality of full cardiac cycles) at different points in time, such as prior to the start of an invasive medical procedure and during an invasive medical procedure in which an interventional medical device 15 is inserted into an guided through the patient.

In an embodiment, the ultrasound image processing apparatus 5 is responsive to an external stimulus 70 indicative of a particular point in the cardiac cycle of the patient such as for example the R-peak of the cardiac cycle. For example, the external stimulus 70 may be provided by a device monitoring the heart rhythm of the patient, such as an ECG recorder or the like. Alternatively, the ultrasound image processing apparatus 5 may be adapted to receive the external stimulus in the form of a raw signal, e.g. a raw ECG signal, and process the raw signal to extract a reference point in the cardiac cycle, such as the R-peak, from the raw signal.

In this embodiment, the ultrasound image processing apparatus 5 is further adapted to trigger the capture of the respective temporal sequences of ultrasound images 150 with an ultrasound probe, i.e. the ultrasound probe is responsive to the ultrasound image processing apparatus 5, such that the different temporal sequences of ultrasound images 150 are synchronized such that each ultrasound image 150 in a particular temporal sequence is captured at the same phase of the cardiac cycle as the ultrasound image 150 in another temporal sequence. Consequently, each temporal sequence 100, 100' comprises a plurality of ultrasound images 150 corresponding to the same phases of the cardiac cycle. As a further consequence, the shape of the anatomical feature of interest 151 between corresponding ultrasound images 150 of different temporal sequences remains largely constant as this shape typically is a function of the phase of the cardiac cycle.

Figure 4:
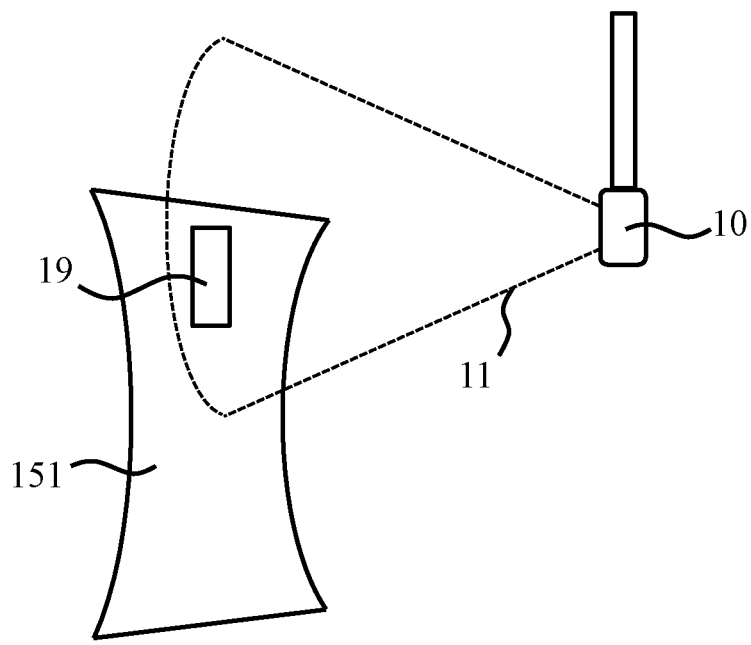
FIG. 4 schematically depicts an imaging arrangement during the initial temporal sequence of ultrasound images.

FIG. 4 and FIG. 5 schematically depict the imaging of an anatomical feature of interest 151 during the same phase of different cardiac cycles with an ultrasound probe 10, as can be recognized from the shape of the anatomical feature of interest 151 being substantially the same in both figures. The ultrasound probe 10 may be positioned on a part of the body of the patient, such as the patient's chest in case of the imaging of the patient's heart. Importantly, during the medical procedure, the ultrasound probe 10 typically remains in the same position on the patient's body such that the ultrasound probe 10 can be considered a stationary source of ultrasound radiation. To this end, the ultrasound probe 10 may be secured in a probe holder or the like to ensure that the ultrasound probe 10 does not move (other than to follow body movements of the patient) during the medical procedure in which the invasive medical device 15 is inserted into the patient's body, e.g. through an artery or vein of the patient's cardiovascular system. Alternatively, the ultrasound probe 10 may be internal to the patient, i.e. inserted into the patient's body, e.g. as part of a further invasive medical device. For example, such an internal ultrasound probe 10 may be an ICE probe, a TEE probe and so on. Where such an internal ultrasound probe 10 is being used, it should be understood that such a probe is typically kept stationary during the capture of the respective temporal sequences of ultrasound images 150 such that different temporal sequences can be directly compared with each other.

In FIG. 4, the generated ultrasound image 150 belongs to the first sequence 100 and in FIG. 5 the generated ultrasound image 150 belongs to the further sequence 100'. This is reflected by the acoustic shadow region 17 cast upon part of the anatomical feature of interest 151 by the presence of the invasive medical device 15 in the ultrasound beam of the ultrasound probe 10 as depicted in FIG. 5, which blocks part of the ultrasound beam 11 from reaching the anatomical feature of interest 151, thereby causing the acoustic shadow region 17 on the anatomical feature of interest 151 as captured in the ultrasound image 150. In contrast, the corresponding region 19 of the anatomical feature of interest 151 in FIG. 4 is clearly visible in the generated ultrasound image 150 due to the absence of the interventional medical device 15 in the first sequence 100' of ultrasound images 150 as explained above. An important insight on which embodiments of the present invention are based is that a merge operation on ultrasound images taken at the same point, i.e. at the same phase, during different cardiac cycles avoids the introduction of motion artefacts caused by the motion of the anatomical feature of interest 151 during the cardiac cycle, as the anatomical feature of interest 151 substantially has the same shape at the same point in time during different cardiac cycles. In contrast, when performing such a merge operation on ultrasound images captured at different phases of the same or different cardiac cycles, such motion artefacts are typically difficult to avoid or compensate for.

Figure 6:
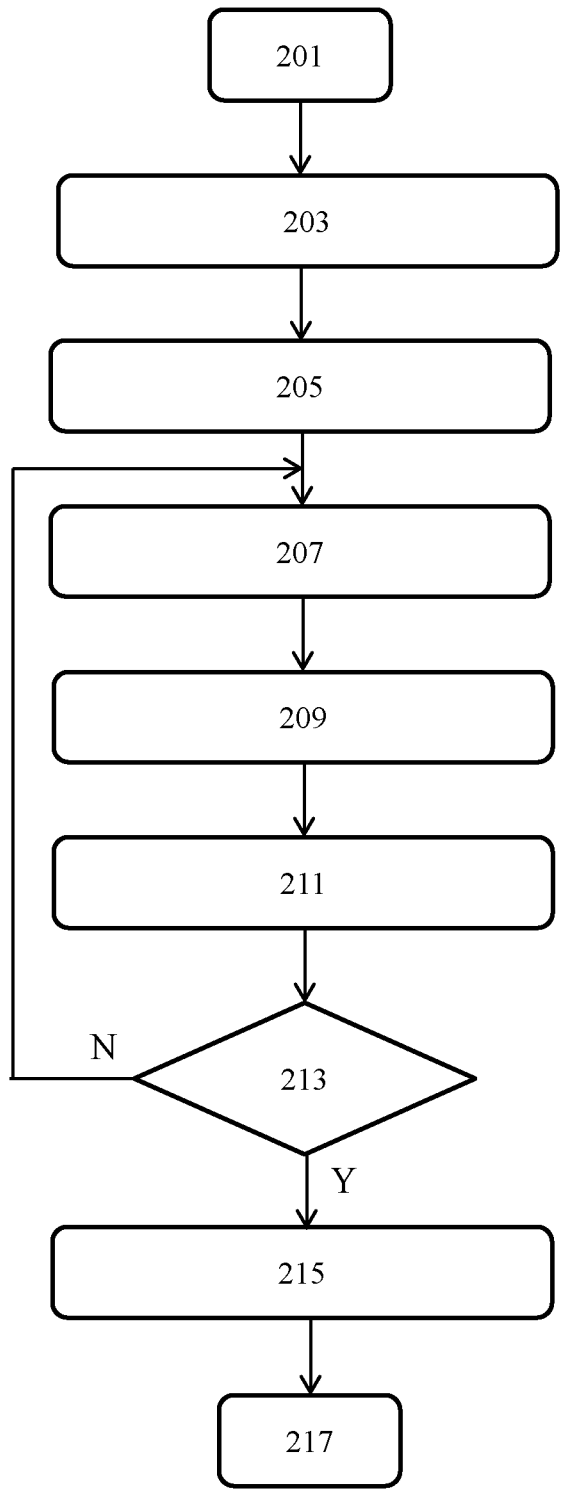
FIG. 6 depicts a flowchart of a method according to an embodiment.

This insight is leveraged by the ultrasound image processor arrangement 50 of the ultrasound image processing apparatus 5 being configured to implement embodiments of the method 200, a flow chart of which is depicted in FIG. 6. The method 200 starts in 201, for example by powering up the ultrasound image processing apparatus 5, after which the method 200 proceeds to operation 203 in which the ultrasound image processing apparatus 5 receives the first sequence 100 of ultrasound images 150, for example in the form of a first cine loop. The first sequence 100 of ultrasound images 150 typically spans exactly one full cardiac cycle or a multiple thereof. As previously mentioned, the first sequence 100 of ultrasound images 150 provides a view of the anatomical feature of interest 151 unimpeded by the invasive medical device 15 such that the view of the anatomical feature of interest 151 does not contain any acoustic shadow regions caused by the invasive medical device 15 blocking part of the ultrasound beam 11 of the ultrasound probe 10. The first sequence 100 of ultrasound images 150 may be captured at any suitable point in time, e.g. before the start of the invasive medical procedure or during the stages of the invasive medical procedure during which the invasive medical device 15 has not yet reached the field of view of the ultrasound probe 10. Other suitable points in time will be apparent to the skilled person. The first sequence 100 of ultrasound images 150 may be directly received from the ultrasound probe 10 or may be retrieved from the data storage arrangement 60 in which the first sequence 100 of ultrasound images 150 has been temporarily stored, e.g. after it has been received from the ultrasound probe 10.

In an embodiment, the recording of the first sequence 100 of ultrasound images 150 may be periodically repeated, e.g. every 20 s or so, to periodically update the first sequence 100 of ultrasound images 150 such that a time difference between recordal of the first sequence 100 of ultrasound images 150 and the further sequence 100' of ultrasound images 150 is minimized, which may reduce the risk of the ultrasound images 150 of the sequences 100, 100' offering different viewing angles of the anatomical feature of interest 151, e.g. due to accidental movement of the ultrasound probe 10 during the invasive medical procedure.

In operation 205, the ultrasound image processing apparatus 5 receives the further sequence 100' of ultrasound images 150, for example in the form of a further cine loop. As with the first sequence 100, the further sequence 100' of ultrasound images 150 typically spans exactly one full cardiac cycle or a multiple thereof such that for each ultrasound image 150 of the first sequence 100, a corresponding ultrasound image 150 is present in the further sequence 100' taken at the same phase of the cardiac cycle such that the anatomical feature of interest 151 has substantially the same shape in both ultrasound images. The difference between such corresponding ultrasound images 150 is that in the ultrasound image 150 belonging to the first sequence 100 the invasive medical device 15 is absent from the field of view of the ultrasound probe 10 whereas in the ultrasound image 150 belonging to the further sequence 100' the invasive medical device 15 or at least a part thereof is visible in the ultrasound image 150 and casts an acoustic shadow region 17 onto the anatomical feature of interest 151, as explained in more detail above with the aid of FIG. 3 and FIG. 4.

In operation 207, the ultrasound image processor arrangement 50 tracks the location of the invasive medical device 15 in the ultrasound images 150 of the further sequence 100' in order to monitor the change in location of the invasive medical device 15 during the monitored cardiac cycle(s). Such location tracking may be implemented in any suitable manner. For example, the invasive medical device 15 may be tracked using in-situ technology, as for instance described in U.S. Pat. No. 9,282,946 B2. Alternatively, the invasive medical device 15 may be tracked using an optical shape sensing algorithm implemented on the ultrasound image processor arrangement 50 in which the shape of the invasive medical device 15 is known to the algorithm such that this shape can be recognized by the algorithm in the ultrasound images 150 of the further sequence 100' and its location determined, e.g. in the form of image coordinates within the ultrasound image 150, by the algorithm.

Figure 7:
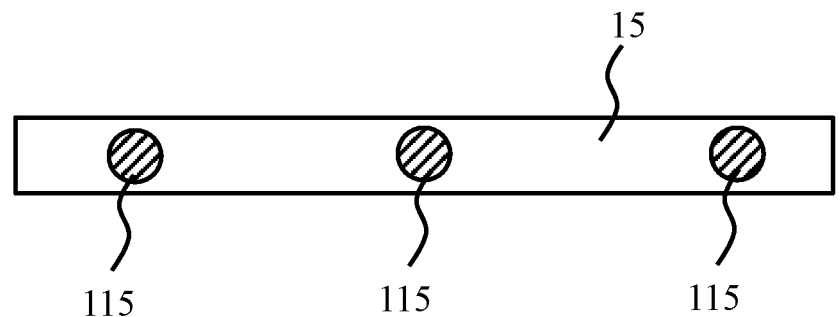
FIG. 7 schematically depicts an invasive medical device for use in embodiments of the present invention.

As a further alternative, the invasive medical device 15 may comprise a plurality of electromagnetic transmitters 115 in a defined spatial arrangement as schematically depicted in FIG. 7, in which case the ultrasound processor arrangement 50 may determine the orientation of the invasive medical device 15 from the received transmissions of the electromagnetic transmitters 115. For example, the electromagnetic transmitters 115 may transmit ultrasound radiation that can be received by the ultrasound probe 10 such that the ultrasound image processor arrangement 50 can determine the positions of the respective electromagnetic transmitters 115 from the received signals by the ultrasound probe 10. As such invasive medical device location techniques are well-known per se, this will not be explained in further detail for the sake of brevity only.

In operation 209, the ultrasound image processor arrangement extracts the image of the invasive medical device 15 from an ultrasound image 150 of the further sequence 100' based on the location of the image of the invasive medical device 15 in this ultrasound image 150 as determined in operation 207. Such an extraction operation for example may be based on the image coordinates of the ultrasound image 150 that were associated with the image of the invasive medical device 15 therein. The extracted image of the invasive medical device 15 is subsequently inserted into the corresponding ultrasound image 150 of the first sequence 100, i.e. into the ultrasound image 150 of the first sequence 100 captured at the same phase of the cardiac cycle as the ultrasound image 150 of the further sequence 100' from which the image of the invasive medical device 15 was extracted.

Figure 8:
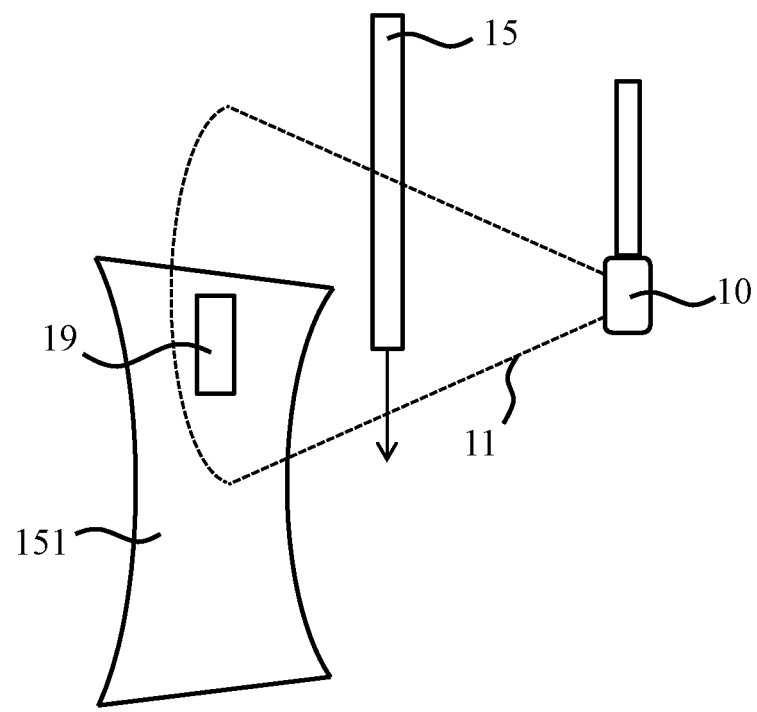
FIG. 8 schematically depicts an ultrasound image resulting from the method according to an embodiment of the present invention.

Consequently, the ultrasound image 150 of the first sequence 100 is augmented as schematically depicted in FIG. 8, in which the invasive medical device 15 extracted from the corresponding ultrasound image 150 of the further sequence 100' is inserted, but the acoustic shadow region 17 is not present, as this ultrasound image 150 was captured in the absence of the invasive medical device 15 in the field of view of the ultrasound probe 10 such that the expected location of the acoustic shadow region 17 shows the non-shadowed region 19 of the anatomical feature of interest 151, thereby yielding a composite or augmented ultrasound image 150 in which the anatomical feature of interest 151 is fully visible in the presence of the invasive medical device 15 in the field of view of the ultrasound probe 10.

This process is repeated for each ultrasound image 150 in the further sequence 100' as symbolized by operation 213, in which it is checked if each ultrasound image 150 of the further sequence 100' has been processed in this manner. If this is not yet the case, the method 200 reverts back to operation 207. Otherwise, the method 200 proceeds to operation 215 in which the ultrasound image processing apparatus 5 controls the display 40 to display the augmented first sequence 100 of ultrasound images 150 of the imaged cardiac cycle(s) of the anatomical feature of interest 151, e.g. an augmented cine loop, in which the invasive medical device 15 has been inserted in each of the ultrasound images 150 based on the determined location of the invasive medical device 15 in the corresponding ultrasound images 150 of the further sequence 100' such that a medical practitioner has a clear view of the anatomical feature of interest 151 in the presence of the invasive medical device 15 in the field of view. Hence, as will be understood from the foregoing, the medical practitioner in fact looks at a pre-recorded sequence 100 of ultrasound images 150 of the anatomical feature of interest 151 such that what is displayed on the display 40 is not the actual (further) sequence 100' of ultrasound images 150 but this augmented pre-recorded sequence 100. The actual sequence 100' is not actually displayed but is used to extract the image of the invasive medical device 15 therefrom, such that only the images of the invasive medical device 15 from this actual sequence 100' are displayed (within the pre-recorded sequence 100) on the display 40.

Figure 9:
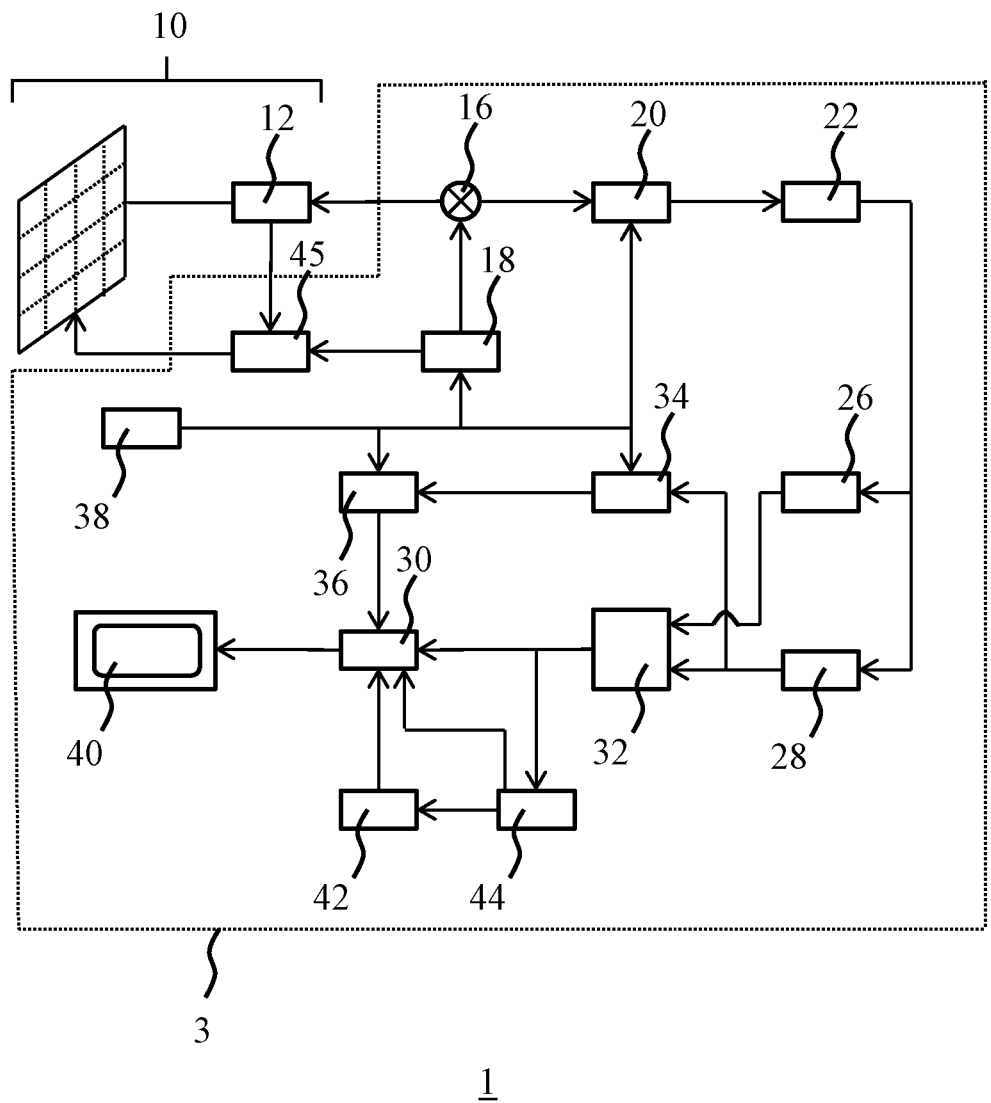
FIG. 9 schematically depicts an ultrasound imaging system according to an example embodiment.

FIG. 9 schematically depicts an example embodiment of an ultrasound imaging system 1 with an ultrasound probe or transducer 10, e.g. an array of ultrasound transducer element tiles (transducer elements) comprising multiple transducer elements, which may be arranged in a one-dimensional or two-dimensional array of transducer cells or elements. Any suitable type of ultrasound transducer elements may be used for this purpose, e.g. piezoelectric transducer (PZT) elements, capacitive micro-machined ultrasound transducer (CMUT) elements, piezoelectric micro-machined transducer (PMUT) elements, and so on, although CMUT elements are particularly preferred, in particular over (PZT) elements due to their superior (adjustable) resonance frequency range, which make CMUT elements particularly suitable for patient monitoring purposes. As such transducer elements are well-known per se, they will not be explained in further detail for the sake of brevity only. The array of transducer cells may be arranged as a phased array to facilitate beam steering of an ultrasound beam generated with the ultrasound transducer 10. Again, such beam steering is well-known per se and will not be explained in further detail for the sake of brevity only. Preferably, the ultrasound transducer 10 has a 2-D array of ultrasound transducer element tiles capable of generating 3-D or volumetric ultrasound images.

The ultrasound probe 10 typically is operable in a transmit mode in which ultrasound beams are generated and a receive mode in which the ultrasound probe 10 is operable to receive echo signals induced by the generated ultrasound beams within the body of the individual being imaged with the ultrasound probe 10. The ultrasound probe 10 typically is controlled by a terminal 3 including the ultrasound image processing apparatus 5. The ultrasound probe 10 may be an external probe, e.g. a TTE probe, or may be an internal probe, e.g. an ICE or TEE probe.

The ultrasound probe 10 may be coupled to a microbeam former 12, which may be integrated in the ultrasound probe 10, which controls transmission and reception of signals by the ultrasound transducer cells (or clusters thereof) of the ultrasound probe 10. Microbeam formers are capable of at least partial beam forming of the signals received by groups or "patches" of transducer element tiles for instance as described in U.S. Pat. No. 5,997,479 (Savord et al.), U.S. Pat. No. 6,013,032 (Savord), and U.S. Pat. No. 6,623,432 (Powers et al.)

The microbeam former 12 may be coupled by a probe cable, e.g. coaxial wire, to the terminal 3, e.g. a patient interface module or the like, comprising a transmit/receive (T/R) switch 16 which switches between transmission and reception modes and protects the main beam former 20 from high energy transmit signals when a microbeam former is not present or used and the ultrasound probe 10 is operated directly by the main system beam former 20. The transmission of ultrasonic beams from the ultrasound probe 10 under control of the microbeam former 12 may be directed by a transducer controller 18 coupled to the microbeam former by the T/R switch 16 and the main system beam former 20, which receives input from the user's operation of the user interface or control panel 38. One of the functions controlled by the transducer controller 18 is the direction in which beams are steered and focused. Beams may be steered straight ahead from (orthogonal to) the ultrasound probe 10, or at different angles for a wider field of view. The transducer controller 18 may be coupled to control the voltage source 45 for the ultrasound transducer array 10. For instance, the power supply 45 may set the DC and AC bias voltage(s) that are applied to CMUT cells in case of a CMUT probe 10, e.g. to operate the one or more CMUT cells of the CMUT elements in collapse mode, as is well-known per se.

The power supply 45 may optionally comprise separate stages for providing the DC and AC components respectively of the stimulus of the CMUT cells, e.g. in transmission mode. A first stage may be adapted to generate the static (DC) voltage component and a second stage may be adapted to generate an alternating variable voltage component having a set alternating frequency, which signal typically is the difference between the overall drive voltage, i.e. stimulus, and the aforementioned static component thereof. The static or bias component of the applied drive voltage preferably meets or exceeds the threshold voltage when forcing the CMUT elements into their collapsed states, i.e. when operating the CMUT elements in collapsed mode. This has the advantage that the first stage may include relatively large capacitors, e.g. smoothing capacitors, in order to generate a particularly low-noise static component of the overall voltage, which static component typically dominates the overall voltage such that the noise characteristics of the overall voltage signal will be dominated by the noise characteristics of this static component.

Other suitable embodiments of the power supply 45 should be apparent, such as for instance an embodiment in which the power supply 45 contains three discrete stages including a first stage for generating the static DC component of the CMUT drive voltage, a second stage for generating the variable DC component of the drive voltage and a third stage for generating the frequency modulation component of the signal, e.g. a pulse circuit or the like. It is summarized that the power supply 45 may be implemented in any suitable manner. It is furthermore emphasized that the power supply 45 is not limited to the operation of CMUT elements; any type of transducer element may be controlled by a suitably adapted power supply 45, as is well-known per se.

The partially beam-formed signals produced by the microbeam former 12 may be forwarded to the main beam former 20 where partially beam-formed signals from individual patches of transducer elements are combined into a fully beam-formed signal. For example, the main beam former 20 may have 128 channels, each of which receives a partially beam-formed signal from a patch of dozens or hundreds of ultrasound transducer cells. In this way the signals received by thousands of transducer cells of a transducer array 10 can contribute efficiently to a single beam-formed signal.

The beam-formed signals are coupled to a signal processor 22, which may form part of the image processor arrangement 50 of the image processing apparatus 5, which in the present embodiment is integrated in the terminal 3 by way of non-limiting example only. The signal processor 22 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and microbubbles.

The signal processor 22 optionally may perform additional signal enhancement such as speckle reduction, signal compounding, and noise elimination. The bandpass filter in the signal processor 22 may be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals may be forwarded to a B-mode processor 26 and optionally to a Doppler processor 28, which processors also may form part of the image processor arrangement 50. The B-mode processor 26 employs detection of an amplitude of the received ultrasound signal for the imaging of structures in the body such as the tissue of organs and vessels in the body. B-mode images of structure of the body may be formed in either the harmonic image mode or the fundamental image mode or a combination of both for instance as described in U.S. Pat. No. 6,283,919 (Roundhill et al.) and U.S. Pat. No. 6,458,083 (Jago et al.)

The Doppler processor 28, if present, processes temporally distinct signals from tissue movement and blood flow for the detection of the motion of substances, such as the flow of blood cells in the image field. The Doppler processor typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material.

This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor may receive and process a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B-mode (and Doppler) processor(s) are coupled to a scan converter 32 and a multiplanar reformatter 44, both which may also form part of the image processor arrangement 50. The scan converter 32 arranges the echo signals in the spatial relationship from which they were received in a desired image format. For instance, the scan converter may arrange the echo signal into a two dimensional (2D) sector-shaped format, or a pyramidal three dimensional (3D) image.

The scan converter can overlay a B-mode structural image with colors corresponding to motion at points in the image field with their Doppler-estimated velocities to produce a color Doppler image which depicts the motion of tissue and blood flow in the image field. The multiplanar reformatter 44 will convert echoes which are received from points in a common plane in a volumetric region of the body into an ultrasonic image of that plane, for instance as described in U.S. Pat. No. 6,443,896 (Detmer). A volume renderer 42, which also may form part of the image processor arrangement 50, converts the echo signals of a 3D data set into a projected 3D image as viewed from a given reference point as described in U.S. Pat. No. 6,530,885 (Entrekin et al.)

The 2D or 3D images are coupled from the scan converter 32, multiplanar reformatter 44, and volume renderer 42 to an image processor 30 forming part of the image processor arrangement 50 for further enhancement, buffering and temporary storage for display on an image display 40. In addition to being used for imaging, the blood flow values produced by the Doppler processor 28 and tissue structure information produced by the B-mode processor 26 are coupled to a quantification processor 34. The quantification processor produces measures of different flow conditions such as the volume rate of blood flow as well as structural measurements such as the sizes of organs and gestational age. The quantification processor may receive input from the user control panel 38, such as the point in the anatomy of an image where a measurement is to be made.

Output data from the quantification processor is coupled to a graphics processor 36 for the reproduction of measurement graphics and values with the image on the display 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name.

The user interface may also be coupled to the transmit controller 18 to control the generation of ultrasound signals from the ultrasound probe 10 and hence the images produced by the transducer array and the ultrasound system. The user interface may also be coupled to the multiplanar reformatter 44 for selection and control of the planes of multiple multiplanar reformatted (MPR) images which may be used to perform quantified measures in the image field of the MPR images.

As will be understood by the skilled person, the above embodiment of an ultrasound imaging system 1 is intended to give a non-limiting example of such an ultrasonic diagnostic imaging system. The skilled person will immediately realize that several variations in the architecture of the ultrasound imaging system 1 are feasible without departing from the teachings of the present invention. For instance, as also indicated in the above embodiment, the microbeam former 12 and/or the Doppler processor 28 may be omitted, the ultrasound probe 10 may not have 3D imaging capabilities and so on. Other variations will be apparent to the skilled person.

The above described embodiments of the method 200 executed by the image processor arrangement 50 may be realized by computer readable program instructions embodied on a computer readable storage medium having, when executed on an image processor arrangement 50 of an ultrasound image processing apparatus 5, e.g. a standalone ultrasound image processing apparatus 5 or an ultrasound image processing apparatus 5 integrated in a user terminal 3, cause the image processor arrangement 50 to implement the method 200. Any suitable computer readable storage medium may be used for this purpose, such as for example an optically readable medium such as a CD, DVD or Blu-Ray disc, a magnetically readable medium such as a hard disk, an electronic data storage device such as a memory stick or the like, and so on. The computer readable storage medium may be a medium that is accessible over a network such as the Internet, such that the computer readable program instructions may be accessed over the network. For example, the computer readable storage medium may be a network-attached storage device, a storage area network, cloud storage or the like. The computer readable storage medium may be an Internet-accessible service from which the computer readable program instructions may be obtained. In an embodiment, the ultrasound image processing apparatus 5 is adapted to retrieve the computer readable program instructions from such a computer readable storage medium and to create a new computer readable storage medium by storing the retrieved computer readable program instructions in a data storage arrangement 60, e.g. in a memory device or the like forming part of the data storage arrangement.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A method of processing a plurality of ultrasound images with an image processor arrangement of an ultrasound image processing apparatus, the method comprising:
    receiving a first sequence of ultrasound images imaging an anatomical feature of interest during a first full cardiac cycle in the absence of an invasive medical device in said ultrasound images, each ultrasound image corresponding to a different phase of said cardiac cycle;
    triggering the capture of a further sequence of ultrasound images in response to an external stimulus indicative of a particular point in a further full cardiac cycle;
    receiving the further sequence of ultrasound images imaging an anatomical feature of interest during the further full cardiac cycle in the presence of the invasive medical device in said ultrasound images, each ultrasound image corresponding to a different phase of said cardiac cycle said invasive medical device at least partially obscuring the anatomical feature of interest, and for each ultrasound image of the further sequence:

tracking the location of the invasive medical device in the ultrasound image;

isolating the invasive medical device from the ultrasound image; and inserting the isolated invasive medical device into an ultrasound image of the first sequence of a corresponding phase of the cardiac cycle in the tracked location; and controlling a display device to display the first sequence of ultrasound images including the inserted invasive medical device, wherein each of the first sequence and further sequence of ultrasound images define a cine loop, and wherein the invasive medical device such as a catheter, a guide wire, and a needle, and so on.

2. The method of claim 1, further comprising determining the location of the invasive medical device in an ultrasound image of the further sequence using an object recognition algorithm.

3. The method of claim 2, wherein the object recognition algorithm is an optical shape sensing algorithm.

4. The method of claim 1, wherein the invasive medical device comprises a plurality of electromagnetic transmitters in a defined alignment along the invasive medical device, the method further comprising determining the location of the invasive medical device in an ultrasound image of the further sequence based on received electromagnetic transmissions from said plurality of electromagnetic transmitters.

5. The method of claim 1, wherein the invasive medical device is one or more of a catheter, a guide wire, and a needle.

* * * * *